US009486424B2

(12) United States Patent
Miller et al.

(10) Patent No.: US 9,486,424 B2
(45) Date of Patent: *Nov. 8, 2016

(54) CREATINE ORAL SUPPLEMENTATION USING CREATINE HYDROCHLORIDE SALT

(71) Applicants: Vireo Systems, Inc., Madison, TN (US); Board of Regents of the University of Nebraska, Lincoln, NE (US)

(72) Inventors: Donald W. Miller, Winnipeg Manitoba (CA); Jonathan L. Vennerstrom, Omaha, NE (US); Mark C. Faulkner, Madison, TN (US)

(73) Assignees: Vireo Systems, Inc., Madison, TN (US); Board of Regents of the University of Nebraska, Lincoln, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/629,532

(22) Filed: Feb. 24, 2015

(65) Prior Publication Data

US 2015/0306051 A1 Oct. 29, 2015

Related U.S. Application Data (60) Continuation of application No. 13/740,909, filed on Jan. 14, 2013, now Pat. No. 8,962,685, which is a division of application No. 12/909,377, filed on Oct. 21, 2010, now Pat. No. 8,354,450, which is a continuation-in-part of application No. 12/477,413, filed on Jun. 3, 2009, now Pat. No. 8,026,385, which is a continuation of application No. 10/846,782, filed on May 14, 2004, now Pat. No. 7,608,641.

(60) Provisional application No. 60/470,356, filed on May 15, 2003.

(51) Int. Cl.

| A61K 31/195 | (2006.01) |
|---|---|
| A61K 31/185 | (2006.01) |
| A23L 1/30 | (2006.01) |
| A23L 1/305 | (2006.01) |
| A61K 31/198 | (2006.01) |
| A61K 31/661 | (2006.01) |
| A23L 2/52 | (2006.01) |
| A23L 1/00 | (2006.01) |

(52) U.S. Cl.
CPC ........ *A61K 31/185* (2013.01); *A23K 20/105* (2016.05); *A23K 20/142* (2016.05); *A23K 50/10* (2016.05); *A23L 1/30* (2013.01); *A23L 1/3051* (2013.01); *A23L 2/52* (2013.01); *A61K 31/195* (2013.01); *A61K 31/198* (2013.01); *A61K 31/661* (2013.01); *A23L 1/0035* (2013.01); *A23V 2002/00* (2013.01)

(58) Field of Classification Search
CPC .................................................. A61K 31/195
USPC ........................................................ 514/565
See application file for complete search history.

(56) References Cited

U.S. PATENT DOCUMENTS

| 3,933,797 | A | 1/1976 | Hamanaka ................. 260/239.1 |
|---|---|---|---|
| 5,627,172 | A | 5/1997 | Almada et al. ............... 514/120 |
| 5,773,473 | A | 6/1998 | Green et al. .................. 514/565 |
| 5,817,329 | A | 10/1998 | Gardiner ....................... 424/439 |
| 5,965,596 | A | 10/1999 | Harris et al. .................. 514/400 |
| 5,973,005 | A | 10/1999 | D'Amelio, Sr. et al. ..... 514/565 |
| 6,136,339 | A | 10/2000 | Gardiner ....................... 424/439 |
| 6,168,802 | B1 | 1/2001 | Howard et al. ............... 424/439 |
| 6,339,819 | B1 | 1/2002 | Huppenthal et al. .......... 712/16 |
| 6,620,425 | B1 | 9/2003 | Gardiner ....................... 424/439 |
| 6,784,209 | B1 | 8/2004 | Gardiner et al. ............. 514/565 |
| 6,897,334 | B2 | 5/2005 | Vennerstrom ................. 560/169 |
| 7,608,641 | B2 | 10/2009 | Miller et al. .................. 514/565 |
| 8,026,385 | B2 | 9/2011 | Miller et al. .................. 560/169 |
| 8,354,450 | B2 | 1/2013 | Miller et al. .................. 514/565 |
| 8,962,685 | B2 * | 2/2015 | Miller .................. A23K 1/1609 514/565 |
| 2002/0150627 | A1 | 10/2002 | Stout et al. .................... 424/601 |
| 2009/0253797 | A1 | 10/2009 | Miller et al. .................. 514/565 |
| 2010/0204204 | A1 | 8/2010 | Zaworotko et al. ..... 514/212.03 |

FOREIGN PATENT DOCUMENTS

| CN | 101407478 | 4/2009 |
|---|---|---|
| WO | WO 0222135 | 3/2002 |

OTHER PUBLICATIONS

Miller, Oral Bioavailability of Creatine Supplements: Is There Room for Improvement. Feb 23, 2010. [Retrieved from the Internet Feb. 12, 2012: URL:http://web.archive.org/web/20100403052353/http://www.concret.com/downloads/CRT_HCI_solutionstability.pdf>]; p. 17-29.

Cross, Camparison of Creatine HCI solution stability to Creatine Monohydrate? Feb. 23, 2010. [Retrieved from the Internet Feb. 12, 2012: URL:http://web.archive.org/web/20100911070855/http://www.concret.com/downloads/CRT_HCI_solutionstability.pdf]; p. 1.

International Search Report dated May 4, 2012 of corresponding International Patent Application No. PCT/US2011/057050.
Non-Final Office Action dated Feb. 20, 2014 of corresponding U.S. Appl. No. 13/740,909.
Final Office Action dated Aug. 14, 2014 of corresponding U.S. Appl. No. 13/740,909.
Non-Final Office Action dated Jun. 13, 2012 of corresponding U.S. Appl. No. 12/909,377.
Final Office Action dated Nov. 2, 2012 of corresponding U.S. Appl. No. 12/909,377.
Non-Final Office Action dated Aug. 18, 2010 of corresponding U.S. Appl. No. 12/477,413.

(Continued)

*Primary Examiner* — Kevin E Weddington
(74) *Attorney, Agent, or Firm* — Smith, Gambrell & Russell, LLP (57) ABSTRACT

The present invention is directed to a third generation form of creatine, specifically a creatine hydrochloride salt, that drives significant improvements in muscle development and recovery due to its enhanced bio-availability, while causing fewer negative side effects compared to previous forms of creatine.

16 Claims, 1 Drawing Sheet

(56) References Cited

OTHER PUBLICATIONS

Final Office Action dated Mar. 22, 2011 of corresponding U.S. Appl. No. 12/477,413.
Non-Final Office Action dated Jul. 2, 2008 of corresponding U.S. Appl. No. 10/846,782.
Final Office Action dated Feb. 6, 2009 of corresponding U.S. Appl. No. 10/846,782.
Non-Final Office Action dated May 12, 2009 of corresponding U.S. Appl. No. 10/846,782.
How CON-CRET™ Works. 2004. [Retrieved from the Internet: https://web.archive.org/web/20041206041250/http://concret.com/howitworks.html].
CON-CRET™ Website. Sep. 8, 2004. [Retrieved from the Internet: https://web.archive.org/web/20040908085346/http://concret.com/order.html].
CON-CRET advertisement. May 27, 2009. [Retrieved from the Internet: http://xwjbb.ghygx.servertrust.com/v/vspfiles/assets/pdf/provensolubility.pdf].
Trademark/Service Mark Application for "CON-CRET," U.S. Appl. No. 78/896,043, US Patent and Trademark Office: TSDR Case Viewer (May 30, 2006).
Invoice from Vireo Systems, Inc. to Biovance, Exhibit 2 of Document 1-3 in *Vireo Systems, Inc. v. Biovance Technologies, Inc.*, Case No. 3:07-cv-00315 in Tennessee Middle District Court filed Mar. 20, 2007, p. 5 (Mar. 31, 2006).
Abdon et al., "On the appearance of phosphocreatine in blood at uraemia," Acta Medica Scandinavica, vol. 95, Issue S90, pp. 444-454 (Jan./Dec. 1938).
Mold et al., "Creatine Ethyl Ether," J. American Chemical Society 77: 178-80(1955).
Gufford et al., "Physiochemical Characterization of Creatine N-Methylguanidinium Salts," Journal of Dietary Supplements, 7(3), p. 240-252 (Aug. 10, 2010).
Bastin et al., "Salt Selection and Optimisation Procedures for Pharmaceutical New Chemical Entities," Org. Process Res. Dev., 4, 427-435 (Jul. 19, 2000).
Hunter, A., Creatine and Creatinine, Monographs on Biochemistry, vol. 8, Longmans, Green and Co, Ltd., p. 36 (1928).
Zumdahl, Steven S., Chemistry, Third Ed., Heath and Company: Lexington MA, 1993. Section 15.6.
Hilal SH et al, Quantitative Treatments of Solute/Solvent Interactions: Theoretical and Computational Chemistry vol. 1, Elsevier, pp. 291-353 (1994).
Needham et al., Solubiltiy of Amino Acids in Pure Solvent Systems. J. Pharm. Sci., 60(4); 565-567 (1971).
Cannan et al., CX V. The Creatine-Creatinine Equilibrium, The Apparent Dissociation Constants of Creatine and Creatinine. Bioch. 59: 920-929 (1928).
MSDS CON-CRET™ Rev. Date: Aug. 18, 2004.
Heymsfield, et al., Assessing Skeletal Muscle Mass: Historical Overview and State of the Art, 5: 9-18 (2014).
Folin and Denis, Protein Metabolism from the Standpoint of Blood and Tissue Analysis: Third Paper. Further Absorption Experiments with Especial Reference to the Behavior of Creatine and Creatinine and to the Formation of Urea, Journal of Biological Chemistry (1912); 12: 141-162.
Benedict and Osterberg, Studies in Creatine and Creatinine Metabolism V. The Metabolism of Creatine, Journal of Biological Chemistry (1923); 56: 229-252.
Chanutin, The Fate of Creatine when Administered to Man, Journal of Biological Chemistry (1926); 67: 29-41.
Pick, Hollinck and Zacharellis, Uber Hem mungs and PotenzierungsPhanomene am quergestreiften Muskel, Arch. exper. Patn u. Phamakol, 220: 83-99 (1953).
Buford, et al., International Society of Sports Nutrition position stand: creatine.supplementation and exercise, Journal of International Society of Sports Nutrition, 4: 6, pp. 1-8 (2007).
Creatinine HCl Data Sheet—Sigma Aldrich.
Jager et al, Analysis of the efficacy, safety, and regulatory status of novel forms of creatine, Amino Acids 40:1369-1383 (2011).
Complaint and accompanying Exhibits, *UNeMed Corp.*, et al. v. *Promera Health, LLC* et al., Case No. 8:15-cv-00135 (D. Neb. Apr. 22, 2015), Doc. #1.
Complaint and accompanying Exhibits, *Promera Health, LLC* v. *Vireo Sys., Inc.* et al., Case No. 8:16-cv-00008 (D. Neb. Feb. 27, 2015), Doc. #1.
Amended Complaint and accompanying Exhibits, *Promera Health, LLC* v. *Vireo Sys., Inc.* et al., Case No. 8:16-cv-00008 (D. Neb. May 20, 2015), Doc. #22.
Second Amended Complaint and accompanying Exhibits, *Promera Health, LLC* v. *Vireo Sys., Inc.* et al., Case No. 8:16-cv-00008 (D. Neb. Jan. 6, 2016), Doc. #57.
Petition and accompanying Exhibits, *Harvest Trading Group, Inc.* v. *Vireo Sys, Inc.* et al., IPR2016-00945 filed on Apr. 22, 2016, Paper No. 1.
Petition and accompanying Exhibits, *Harvest Trading Group, Inc.* v. *Vireo Sys, Inc.* et al., 1PR2016-00947 filed on Apr. 22, 2016, Paper No. 1.

\* cited by examiner

CREATINE ORAL SUPPLEMENTATION USING CREATINE HYDROCHLORIDE SALT

CROSS-REFERENCE TO RELATED APPLICATIONS

This is a divisional of U.S. patent application Ser. No. 12/909,377, filed Oct. 21, 2012, now U.S. Pat. No. 8,354,450, which is a continuation-in-part of U.S. patent application Ser. No. 12/477,413, filed Jun. 3, 2009, now U.S. Pat. No. 8,026,385, which is a continuation of U.S. patent application Ser. No. 10/846,782, filed May 14, 2004, now U.S. Pat. No. 7,608,641, which claims priority to U.S. Provisional Application 60/470,356, filed May 15, 2003, the entirety of which is incorporated herein.

FIELD OF THE INVENTION

The present invention is directed to a form of creatine that has increased aqueous solubility, increased plasma uptake at low dosage amounts, and improved stability and half-life. In particular, the present invention relates to a creatine supplement that, when compared to creatine monohydrate, has an increased aqueous solubility of at least an order of magnitude, a bioavailability or plasma uptake level of at least 50 percent greater than creatine monohydrate, and a shelf-life of more than double the shelf-life of creatine monohydrate.

BACKGROUND OF THE INVENTION

Creatine is a naturally occurring nitrogenous compound found in the skeletal muscles of vertebrates that plays an important role in protein metabolism and other bio-chemical functions. For example, creatine is taken up into muscle cells by specific receptors and converted to phosphocreatine by creatine kinase.

Both creatine and phosphocreatine play an important role in the anaerobic production of ATP during short and intensive exertions, via the creatine kinase system. Specifically, during muscle contraction, there is an increase in the amount of phosphocreatine (which is generated from creatine) and consequently in ATP. The amount of phosphocreatine in the muscle cell determines the amount of time it takes for a muscle to recover from activity; thus, supplementing the diet with creatine can increase the concentration of phosphocreatine in muscles by 6 percent to 16 percent, with a consequent increase in the ATP turnover during physical exertion.

Creatine-containing supplements have been shown to increase lean body mass, high intensity power output, and overall physical strength. By virtue of these characteristics, creatine has met with enormous success among professional and recreational athletes, as well as professional and amateur bodybuilders, in recent years as a dietary supplement.

Increasing creatine levels in muscle through dietary supplementation has proven effective at enhancing athletic performance, increasing muscle workload and shortening muscle recovery time. In addition, there is increasing interest in creatine dietary supplements for a variety of therapeutic indications, including muscular dystrophy, cardiovascular diseases, neurodegenerative disorders, and mental retardation. The zwitterionic creatine monohydrate has been the standard creatine salt of choice for commercial creatine supplement formulations.

However, creatine supplements containing creatine monohydrate are not ideal dietary supplements due to their low aqueous solubility. In other words, relatively large doses of creatine monohydrate must be consumed with large amounts of fluid for effective use. People often experience excessive water retention (bloating), cramps, and significant gastrointestinal problems due to the large dosages. In addition, the relatively high doses of creatine monohydrate required to produce the desired biological effects suggest that the oral bioavailability of creatine monohydrate is low and that more efficient dosage forms may provide better desired results accompanied by fewer gastrointestinal side effects.

There are other known salt forms of creatine including creatine citrate (creatine effervescent) and creatine pyruvate that have been patented and marketed as improvements over creatine monohydrate. However, despite the various salt forms currently marketed, there remains a need in the art for a more improved form of creatine with improved solubility and bioavailability characteristics that can be consumed in smaller dosage forms.

SUMMARY OF THE INVENTION

The present invention is directed to a supplement that includes creatine HCl, wherein the creatine HCl possesses a solubility of at least 600 mg/mL in water at 25° C. In one embodiment, the creatine HCl is at least 95 percent free of contaminants. In another embodiment, the recommended dosage range for the creatine HCl is between about one quarter teaspoon to about one tablespoon per hundred pounds body weight.

In this aspect of the invention, the supplement may be being taken orally. In one embodiment, the creatine HCl has a shelf-life of at least about 45 days in aqueous solution at room temperature. In another embodiment, an effective dosage of the supplement is about 500 mg to about 1500 mg of creatine HCl per 100 pounds body weight. In yet another embodiment, the creatine HCl further comprises an additive or feed supplement for livestock.

The present invention is also directed to a formula used to enhance athletic performance including creatine HCl, wherein the creatine HCl exhibits an aqueous solubility that is at least about 15 times greater than that of creatine monohydrate. In one embodiment, the formula also includes additional species of creatine selected from the group comprising creatine esters, creatine pyruvate, creatine phosphate, creatine alpha-ketoglutarate, creatine citrate, and combinations thereof. In another embodiment, the formula also includes additional supplements selected from the group comprising carbonate salts, methylsulfonylmethane, glucosamine, and chondroitin.

In yet another embodiment, the formula also includes compounds selected from the group comprising proteins, amino acid supplements, carbohydrates, D-Ribose, fats, fiber and combinations thereof. In still another embodiment, the formula also includes sweeteners selected from the group comprising sucralose, aspartame, saccharin, acesulfame potassium, neohesperidin dihydrochalcone, glycyrrhizin, thaumatin, alitame, stevioside, and combinations thereof. In one embodiment, the formula further includes a supplement selected from the group comprising sports bars, nutritional bars, powders, liquids, gels, sports drinks, and beverages. In another embodiment, the formula also includes flavoring agents selected from the group comprising cocoa, yogurt, peanut butter, mint, cheesecake, hazelnut paste, almonds, granola, coconut, strawberry, banana, cherry, plum, raspberry, lemon, orange, lime, pineapple, blueberry and other fruit flavors, coffee, or cremes and jellies, and combinations thereof.

The present invention is also directed to a granular powder including a creatine HCl product formed by the reaction of an alcohol, an acid catalyst, and creatine monohydrate, wherein the solubility of the creatine HCl product is at least about 650 mg/ml.

In this aspect of the invention, the alcohol may be selected from the group consisting of ethanol, methanol, butanol, and isopropanol. In one embodiment, the reaction is a super-saturated reaction including ethanol, acetyl chloride, and creatine monohydrate. In one embodiment, the volume of ethanol used is between about 4 and 5 L per kg of creatine monohydrate and the quantity of acetyl chloride used is between about 1.0 to about 1.1 mole equivalents of creatine monohydrate.

In another embodiment, the super-saturated reaction further includes the steps of mixing the alcohol and acetyl chloride in a reactor that is cooled to between about 0° C. and 20° C.; allowing the temperature of the reactor to increase to about 38° C.; adding creatine monohydrate; and maintaining a temperature of between about 30° C. and about 40° C. The creatine HCl product is preferably at least 95 percent free of contaminants.

BRIEF DESCRIPTION OF THE DRAWINGS

Further features and advantages of the invention can be ascertained from the following detailed description that is provided in connection with the drawing(s) described below.

DETAILED DESCRIPTION OF THE INVENTION

The present invention is directed to a third generation form of creatine, specifically a creatine hydrochloride salt ("creatine HCl") that has improved aqueous solubility, plasma uptake, and shelf-life over that of previous forms of creatine. The present invention further contemplates suitable methods to produce the creatine HCl in a granular precipitate form with high purity and yield.

The creatine HCl of the present invention may be used as a nutritional supplement for enhancing muscle performance and muscle mass in both humans and livestock, including muscle quality in livestock. In this regard, based on the known beneficial qualities of creatine with regard to muscle development and recovery, it is believed that the improvements in solubility and plasma uptake of the creatine HCl of the present invention also lead to significant improvements in muscle development and recovery as compared to creatine monohydrate. Moreover, without being bound to any particular theory, the improvements in the solubility and plasma uptake also reduce or essentially eliminate the negative side effects typically associated with previous forms of creatine.

Creatine HCl Solubility

The creatine HCl of the present invention represents an improvement on prior forms of creatine due to is its remarkably high aqueous solubility. As the low oral absorption of creatine supplements are believed to be attributable at least in part to reduced solubility, the creatine HCl of the present invention is also expected to have better oral absorption properties compared to other forms of creatine.

The creatine HCl of the invention preferably has an aqueous solubility of at least about 150 mg/ml at room temperature. In one embodiment, the creatine HCl preferably possesses an aqueous solubility at room temperature of about 240 mg/mL or greater, more preferably of about 480 mg/mL or greater, and more preferably of about 800 mg/mL or greater. In another embodiment, the aqueous solubility of the creatine HCl of the invention ranges from about 250 mg/ml to about 1000 mg/ml. In yet another embodiment, the creatine HCl has an aqueous solubility of about 400 mg/ml to about 1000 mg/ml. In still another embodiment, the aqueous solubility of the creatine HCl of the invention is at least about 650 mg/ml, preferably at least about 675 mg/ml. For example, the aqueous solubility of the creatine HCl is preferably 679±18 mg/ml when tested at room temperature (25° C.) after a time period of about 1.5 hours.

In comparison, the aqueous solubility of other forms of creatine including creatine monohydrate and creatine citrate salt typically ranges from about 10 to about 16 mg/mL. Accordingly, the creatine HCl of the present invention exhibits an aqueous solubility that is at least about 15 times greater than that of creatine monohydrate. In one embodiment, the aqueous solubility of the creatine HCl is at least about 20 times greater than that of creatine monohydrate, preferably at least about 30 times greater than that of creatine monohydrate. In another embodiment, the creatine HCl has an aqueous solubility that is at least about 40 times greater than that of creatine monohydrate, preferably at least about 50 times greater than that of creatine monohydrate. For example, the aqueous solubility of the creatine HCl is preferably 42 times greater than that of creatine monohydrate when tested at room temperature (25° C.) after a time period of about 1.5 hours.

Creatine HCl Bioavailability

The creatine HCl of the present invention exhibits improved bioavailability compared to creatine monohydrate. As used herein, the term "bioavailability" refers to the rate and amount of a drug (or in this case a supplement) that reaches the systemic circulation of a patient following administration of the drug or prodrug thereof to the patient. Accordingly, bioavailability is one of the principal pharmacokinetic properties of drugs and can be determined by evaluating, for example, the plasma or blood concentration-versus-time profile for a drug. Parameters useful in characterizing a plasma or blood concentration-versus-time curve include the area under the curve (AUC), the maximum drug concentration ($C_{max}$), and the time to maximum concentration ($T_{max}$).

As used herein, the term "AUC" refers to the area under a curve representing the concentration of a compound or metabolite thereof in a biological fluid, e.g., plasma and blood, in a patient as a function of time following administration of the compound to the patient. The AUC may be determined by measuring the concentration of a compound or metabolite thereof in a biological fluid using methods such as liquid chromatography-tandem mass spectrometry (LC/MS/MS), at various time intervals, and calculating the area under the plasma concentration-versus-time curve. Suitable methods for calculating the AUC from a drug concentration-versus-time curve are well known in the art.

$C_{max}$ is the maximum concentration of a drug in the plasma or blood of a patient following administration of a dose of the drug or form of drug to the patient. $T_{max}$ is the time to the maximum concentration ($C_{max}$) of a drug in the plasma or blood of a patient following administration of a dose of the drug or form of drug to the patient.

By definition, when a medication is administered intravenously, its bioavailability is 100 percent. However, when a medication is administered via other routes (such as orally), its bioavailability decreases (due to incomplete absorption and first-pass metabolism). More specifically, bioavailability is a measure of the ratio of the amount of drug "absorbed" from a test formulation to the amount "absorbed" after administration of a standard formulation. Frequently, the "standard formulation" used in assessing bioavailability is the aqueous solution of the drug, given intravenously.

The amount of drug absorbed is taken as a measure of the ability of the formulation to deliver drug to the sites of drug action; obviously—depending on such factors as disintegration and dissolution properties of the dosage form, and the rate of biotransformation relative to the rate of absorption—dosage forms containing identical amounts of active drug may differ markedly in their abilities to make drug available, and therefore, in their abilities to permit the drug to manifest its expected pharmacodynamic and therapeutic properties. The "amount absorbed" is conventionally measured by one of two criteria, either the area under the time-plasma concentration curve (AUC) or the total (cumulative) amount of drug excreted in the urine following drug administration.

A linear relationship exists between the AUC and dose when the fraction of the drug absorbed is independent of dose, and elimination rate (half-life) and volume of distribution are independent of dose and dosage form. However, when AUC is dependent on dose, as occurs when, for example, there is saturable absorption, significant metabolism, or poor solubility of the drug in the GI tract, a non-linear relationship exists between AUC and dose.

In order to compare the relative bioavailability of various forms of creatine and to correct for the slightly different doses of creatine administered with various forms due to the different molecular weights of the salt forms, the AUC plasma uptake values observed for creatine monohydrate and creatine HCl are entered into the following equation to produce a ratio:

$$\frac{(AUC_{SampleA} * Dose_B)}{AUC_{SampleB} * Dose_A}$$

Based on this relationship, the relative bioavailability of creatine HCl to creatine monohydrate is preferably about 1.5 or greater, more preferably about 1.55 or greater, and even more preferably about 1.65 or greater. In one embodiment, the ratio is about 1.70 or greater.

In other words, the relative bioavailability of creatine HCl is preferably about 50 percent greater than creatine monohydrate, more preferably about 55 percent greater than creatine monohydrate and most preferably about 60 percent greater than creatine monohydrate. In one embodiment, the bioavailability of the creatine HCl is at least about 65 percent greater than bioavailability of creatine monohydrate. In another embodiment, the creatine HCl has a bioavailability of at least about 70 percent greater relative to creatine monohydrate.

Creatine HCl Stability

The half-life of other known forms of creatine in blood plasma is short (approximately 1-1.5 hours). Thus, to be effective, the creatine formulation must be able to reach desired blood plasma levels rapidly. In view of the bioavailability of previously known forms of creatine, such desired blood plasma levels can be obtained only by the administration of high doses of creatine, e.g., 5 to 10 g for mean body weights of about 70 kg.

In contrast, the creatine HCl of the invention is able to obtain high blood plasma levels at low doses at least in part due to its increased stability. In addition, due to the overall increase in stability, the creatine HCl of the invention is capable of maintaining a minimal creatine blood serum level for longer periods of time, thereby enhancing an individual's muscle performance.

With regard to latent product storage, standard shelf-life according to the FDA is considered to be the time it takes for 10 percent of the starting material to degrade in a given sample. Creatine monohydrate typically exhibits a shelf-life of about one week when stored in aqueous solution at room temperature. In contrast, the creatine HCl of the present invention possesses a shelf-life of about 45 days or greater in aqueous solution. In one embodiment, the shelf-life of the creatine HCl of the invention in aqueous solution is at least about 60 days, preferably at least about 75 days. In another embodiment, the creatine HCl of the invention possesses a shelf-life of about 90 days or greater in aqueous solution.

As will be understood by those of ordinary skill in the art, higher temperatures accelerate degradation of all forms of creatine, including the creatine HCl of the invention. However, when exposed to higher temperatures, creatine monohydrate still degrades at a much higher rate than creatine HCl. In one embodiment, the shelf life of creatine HCl in aqueous solution at a temperature ranging from about 10 to 20 degrees (° C.) higher than room temperature is at least about 14 days, preferably at least about 25 days, and more preferably at least about 30 days. In another embodiment, the shelf life of the creatine HCl at 50° C. is at least about 1 day, preferably at least about 2 days, and more preferably at least about 5 days.

Supplement Forms

Due to its enhanced properties, the effective dose of creatine HCl is much less than other forms of creatine. In order to increase muscle mass and strength, compositions of creatine monohydrate are generally dosed in an amount from about 5 g to about 10 g per 150 pounds body weight. Contrastingly, in one embodiment of the present invention, the effective dose may range from about one quarter teaspoon to about one tablespoon per hundred pounds body weight, more preferably between about one quarter teaspoon to about one teaspoon per hundred pounds body weight, and most preferably between about one quarter teaspoon to about one half teaspoon per hundred pounds body weight.

In this aspect of the invention, the effective dose may range from about 500 mg to about 1500 mg per 100 pounds body weight. For example, in one embodiment, the effective dose may be from about 1500 mg to about 3000 mg for a subject that weighs up to 250 pounds. In one embodiment, the effective dose is from about 2250 mg to about 4500 mg for a subject that weighs over 250 pounds. In another embodiment, the effective dose is from about 750 mg to about 1500 mg per 100 pounds body weight.

In comparison to creatine monohydrate, the effective dose of creatine HCl is at least about 50 percent less than the effective dose of creatine monohydrate. In another embodiment, the effective dose of creatine HCl is at least about 55 percent less than the effective dose of creatine monohydrate. In yet another embodiment, the effective dose of creatine HCl is at least about 60 percent less, preferably at least about 65 percent less, than the effective dose of creatine monohydrate. For example, the effective dose of creatine HCl is preferably about 70 percent less than the effective dose of creatine monohydrate.

In one embodiment of the invention, creatine HCl may be provided in a liquid, gel, or powder form, with powders suitable for mixing with water or other liquids being preferred. These formulations may be added into a beverage. In addition, the creatine HCl may be provided as an ingredient premixed in a beverage. Examples of beverages contemplated by the invention include, but are not limited to, sports drinks and liquid meal replacements.

In addition to the sports beverage area, various other applications for use with creatine HCl are contemplated by the present invention, and may include its application, in functional food supplements, including so-called "athletic bars" and "sports bars."

It is contemplated that the creatine HCl may be combined with any or all of the following compounds: proteins, amino acid supplements, complex carbohydrates, D-Ribose, fats and fiber. Suitable sources of proteins in the present invention may include proteins derived from milk, whey protein, hydrolyzed beef protein, casein and salts thereof. Other preferred proteins may include peanut protein, wheat protein, egg protein, leptin, and vegetable proteins, such as soy protein. The hydrolyzed beef protein may be bovine bone gelatin.

In various embodiments of the invention, fats may be used to provide long term energy. Fats useful in the present invention may include, but are not limited to, cocoa butter, milk fat, vegetable oil, hydrogenated vegetable oils, such as hydrogenated palm oil, hydrogenated shea oil, hydrogenated cottonseed oil, hydrogenated coconut oil, hydrogenated corn oil, hydrogenated soybean oil, and hydrogenated peanut oil; caprocaprylbehenin; monounsaturated fats such as olive oil and canola oil, sunflower and safflower oils; fish and marine fats.

In addition, fats containing linoleic and linoleic esters have nutritionally desirable features and are thus contemplated for inclusion in the composition of the invention. Moreover, polyols, such as sugar alcohols, may be used in the formulation. Non limiting examples of suitable polyols for use with the present invention include hydrogenated isomaltulose, maltitol, sorbitol, lactitol, erythritol, mannitol, xylitol, polydextrols, and mixtures thereof. Glycerin might, under certain definitions, be included among the polyols, but for the purpose of the present invention, we classify it separately.

Carbohydrates for fast energy for us with the present invention may include, but are not limited to, glucose, fructose, galactose, sucrose, lactose, maltose, ribose, and combinations thereof. Other carbohydrates suitable for use in the invention may include, but are not limited to, starches, glycogen, fibers, cellulose, beta glucan, pectin, guar gum, and mixtures thereof.

Sweeteners and flavoring agents may be added individually or in combination to improve or alter the taste of the creatine HCl formula, functional food supplement, or beverage. Sweeteners appropriate for use in the present invention are preferably, non-nutritive sweeteners, and may include sucralose, aspartame, saccharin, and acesulfame potassium. Other sweeteners may include neohesperidin dihydrochalcone, glycyrrhizin, thaumatin, alitame, and stevioside. Flavoring agents may include cocoa or yogurt, which may be used in combination with vanillin or vanilla extract. Other preferred flavoring agents may include peanut butter, mint, cheesecake, hazelnut paste, almonds, granola, coconut, strawberry, banana, cherry, plum, raspberry, lemon, orange, lime, pineapple, blueberry and other fruit flavors, coffee, or cremes and jellies, and combinations thereof.

The present invention is also directed to creatine HCl compositions that also contain other forms of creatine, carbonate salts, methylsulfonylmethane, glucosamine (preferably used in the form of the salt with hydrochloric, sulfuric, phosphoric, or other biocompatible acid), chondroitin, or combinations thereof. When creatine HCl is combined with other forms of creatine, it is envisioned that creatine HCl will account for greater than 50 percent of the total creatine in the composition. Other forms of creatine appropriate for use with creatine HCl include creatine esters, creatine pyruvate, creatine phosphate, creatine alpha-ketoglutarate, creatine citrate, and combinations thereof.

The creatine HCl of the present invention can also be used as a feed additive in livestock to further enhance the energy requirements of companion animals, sporting and gaming animals, livestock, and other animals, as may be desired and required. In particular, creatine HCl may have immediate applications in the solid oral dosage supplementation area, as an additive or a feed supplement for such animals. Or, it may be added into any liquid that is consumed by such animals.

It is contemplated that the oral supplementation of this invention may be provided in a solid oral dosage form, such as in a capsule form, for treatment requirements when taken by a human, animal, and the like. Oral dosage forms encompass tablets, dragees, and capsules. In addition, the creatine HCl may be in a form that can be administered rectally, such as a suppository. Other dosage forms include suitable solutions for administration topically, parenterally or orally, and compositions which can be administered buccally or sublingually.

In one embodiment, the supplement may be a combination of a powder and a solid oral dosage form. In this regard, the amount of creatine HCl in the supplement is preferably about 500 mg to about 2000 mg (inclusive of any binders, sugars, fillers or excipients). For example, the supplement may contain from about 700 mg to about 1500 mg, preferably at least about 750 mg (inclusive of any binders, sugars, fillers or excipients).

When the creatine HCl of the invention is in a solid oral dosage form, the tablet, dragee, or capsule may include about 500 mg to about 2000 mg of creatine HCl (inclusive of any binders, sugars, fillers or excipients). In one embodiment, the solid oral dosage form includes from about 750 mg to about 1750 mg (inclusive of any binders, sugars, fillers or excipients). In another embodiment, the solid oral dosage form includes from about 1000 mg to about 1500 mg (inclusive of any binders, sugars, fillers or excipients). In yet another embodiment, the solid oral dosage form includes at least about 1250 mg creatine HCl (inclusive of any binders, sugars, fillers or excipients).

In another aspect of the invention, the creatine HCl is combined with another supplement in a solid oral dosage form. For example, the creatine HCl may be combined with HMB, L-glutamine, ribose, or combinations thereof in a solid oral dosage form. In one embodiment, the creatine HCl is included in a solid oral dosage form that includes at least one other supplement in an amount of about 100 mg to about 500 mg. In another embodiment, the creatine HCl is included in the solid oral dosage form that includes at least one other supplement in an amount of about 150 mg to about 400 mg. In yet another embodiment, the creatine HCl is included in the solid oral dosage form that includes at least one other supplement in an amount of about 150 mg to about 300 mg. For example, the creatine HCl may be included in a solid oral dosage form that includes at least one other supplement in an amount of about 200 mg.

In general, in addition to the active compound, i.e., creatine HCl, the pharmaceutical compositions of this invention may contain suitable excipients and auxiliaries that facilitate processing of the active compounds into preparations which can be used pharmaceutically. Nonlimiting examples of suitable excipients include fillers such as calcium phosphates (e.g., tricalcium phosphate or calcium hydrogen phosphate) and binders such as starch, paste, using, for example, maize starch, wheat starch, rice starch, potato starch, gelatin, gum tragacanth, vegetable cellulose such as methyl cellulose, ethyl cellulose, hydroxypropyl cellulose, hydroxypropylmethyl cellulose sodium carboxymethylcellulose, and hydroxyethyl methyl cellulose, and/or polyvinyl pyrrolidone.

If desired, disintegrating agents may also be added, such as the above-mentioned starches as well as carboxymethyl starch, cross-linked polyvinyl pyrrolidone, agar, or alginic acid or a salt thereof, such as sodium alginate. Flow-regulating agents and lubricants are also contemplated for use with the creatine HCl and include, but are not limited to silica, talc, stearic acid or salts thereof, such as magnesium stearate or calcium stearate and/or polyethylene glycol.

When a polyethylene glycol (PEG) component is used, the PEG may have an average molecular weight of about 1000 to about 9000. Commercially available forms of such PEGs are available under the tradename Carbowax® PEG 3350, PEG 1450, PEG 4000, PEG 4600, PEG 8000, and PEG 6000.

Dragee cores may be provided with suitable coatings which, if desired, may be resistant to gastric juices. For this purpose, concentrated sugar solutions may be used, which may optionally contain gum arabic, talc, polyvinylpyrrolidone, polyethylene glycol and/or titanium dioxide, lacquer solutions and suitable organic solvents or solvent mixtures, and combinations thereof. In order to produce coatings resistant to gastric juices, solutions of suitable cellulose preparations such as acetylcellulose phthalate or hydroxypropylmethylcellulose phthalate, dyestuffs and pigments may be added to the tablet of dragee coatings, for example, for identification or in order to characterize different combinations of compound doses.

Furthermore, the composition could be added as a fortification to other foods.

Methods of Making

A granular precipitate consisting of the creatine HCl of the invention in high purity and yield may be formed from the reaction of creatine monohydrate and a solvent that is infused with HCl. Any solvent that dissolves the creatine monohydrate and precipitates creatine hydrochloride may be employed. In one embodiment, the solvent employed is an alcohol. For example, the solvent may be ethanol. Other alcohols suitable for use in the present invention include short chain alcohols selected from methanol, propanol, butanol, isopropanol, and the like. In addition, acetonitrile is contemplated for use as a suitable solvent in the context of the present invention.

The acid catalyst may be any acid catalyst that can be added to a solvent to produce a solution of dissolved HCl. Other non-limiting examples of suitable acid catalysts include acyl chlorides having the general structure: R—CO—Cl, where R is an organic radical group. For example, other acid catalysts contemplated for use with the present invention include acetyl chloride, benzoyl chloride, and (chlorocarbonyl) acetic acid. In addition, phosphorus chlorides, thionyl chloride ($SOCl_2$) are contemplated for use in accordance with the present invention. Moreover, the HCl may be generated by the reaction of sulfuric acid and sodium chloride.

The yield of creatine HCl produced in each reaction can be determined by 1H-NMR analysis used for organic chemicals or other standard methods known in the art. As known to those of ordinary skill in the art, 1H-NMR uses spectroscopy and nuclear magnetic resonance technology to ascertain the structure of chemical compounds.

Preparations of the creatine HCl of the present invention are preferably at least about 80 percent pure, preferably at least about 95 percent pure, more preferably at least about 97 percent pure, and even more preferably at least about 99 percent pure. For example, a preparation of creatine HCl in accordance with the present invention may be about 98 to 99 percent pure. The term "pure" as used herein refers to the lack of impurities in the preparation. The main impurities typically detected in the composition are creatine ethyl ester hydrochloride and creatinine hydrochloride.

In one embodiment, the creatine HCl of the present invention is made as a super-saturated batch that results in yields at least about 139 percent greater than those achieved with described techniques. In order to produce a super-saturated batch of creatine HCl, a solvent and an acid catalyst are combined in a reactor that is cooled to between about 0° C. and about 20° C. Following addition of the acid catalyst, the reactor temperature is allowed to return to approximately 38° C., at which time the creatine monohydrate can be added. The optimum temperature for the reaction is preferably between about 30° C. and about 40° C., more preferably between about 32° C. and 38° C., and most preferably between 35° C. and 37° C. One additional advantage of the super saturated batch technique is that it requires much less solvent compared to other techniques.

For example, a super-saturated batch of creatine HCl may include between about 1.0 and about 1.1 mole equivalents of acetyl chloride to creatine monohydrate, and preferably between 4 and 5 L of solvent, preferably ethanol, per kg of creatine monohydrate used. In one embodiment, the batch is formed from about 1.0 to about 1.1 mole equivalent creatine monohydrate and about 1.0 to about 1.1 mole equivalent of acetyl chloride dissolved in about 1 ml to about 5 ml ethanol (per gram of creatine monohydrate). A preferred example of a super-saturated batch of creatine HCl can be made using about 410 L of ethanol, about 27.2 kg of acetyl chloride, and about 100 kg of creatine monohydrate.

In another embodiment, 1.4 mole equivalents of acetyl chloride are dissolved in ethanol to form the solvent. In fact, above 1.5 and including 2.0 mole equivalents acetyl chloride, the process produces less desirable creatine ethyl ester hydrochloride at a sacrifice of yield for creatine hydrochloride. And, above 2.0 mole equivalents acetyl chloride, the process forms creatinine hydrochloride. The amount of ethanol employed may vary between about 6 mL to about 10 mL, preferably 10 ml. The temperature of the solution may be raised to between about 24° C. to about 50° C., preferably from about 25° C. to about 35° C. In one embodiment, the temperature of the solution is raised to 25° C. In fact, at temperatures above the preferred range, the process produces the less desirable creatine ethyl ester hydrochloride and, in excess of 50° C., the process produces increased amounts of undesirable creatinine hydrochloride. The conditions result in precipitation of a hydrochloride salt of creatine in granular form in the vessel. After reducing the temperature and pressure to ambient atmospheric temperature and pressure, the manufacturer may collect the granules of creatine HCl and package the granules for consumption by humans or livestock after filtering and washing with a solvent such as ethanol. An alternate embodiment of the process uses anhydrous creatine.

In yet another embodiment, a manufacturer may produce creatine HCl by bubbling gaseous hydrochloric acid into diethyl ether solvent. Then, about 0 grams to about 5 grams of creatine monohydrate is stirred into the solvent at 25° C. for two hours. From the reaction, creatine HCl precipitates. The manufacturer then filters and washes the precipitate with 50 mL of fresh diethyl ether. Lastly, the precipitate dries at room temperature and/or in a heated and/or vacuumed dryer to a crystalline form, white in color and then is packaged for human or livestock consumption. In using the alternative method, the hydrochloric acid may have a range of concentrations so long as the hydrochloric acid exceeds the molar equivalent of creatine monohydrate.

Starting materials useful for preparing compounds and intermediates thereof, and/or practicing methods described herein are commercially available or can be prepared by well-known synthetic methods.

EXAMPLES

The following non-limiting examples are merely illustrative of the preferred embodiments of the present invention, and are not to be construed as limiting the invention, the scope of which is defined by the appended claims.

Example 1

Creatine monohydrate and the creatine hydrochloride of the present invention were assessed for relative solubility, and thus bio-availability. The results are shown in Table 1.

TABLE 1

|  | Creatine Monohydrate | Creatine Hydrochloride |
| --- | --- | --- |
| Solubility (at 62° F.) | 0.015 g/mL | 0.888 g/mL |
| Relative Solubility (compared to creatine monohydrate) | 1.0 | 59.2 |

For the creatine monohydrate sample: 5 grams of creatine monohydrate were added to 100 mL of water at room temperature and stirred for 2 minutes. The solution was filtered, and then dried and massed to determine the amount of sample remaining un-dissolved.

For the creatine hydrochloride sample: 50 grams of creatine hydrochloride were added to 100 mL of water at room temperature and stirred for 2 minutes. At that time, another 40 grams (4 doses of 10 g each) until the water remained cloudy at the end of the 2 minute stirring period. The solution was filtered, and then dried and massed to determine the amount of sample remaining un-dissolved.

Example 2

The saturated solubilities of creatine HCl and creatine monohydrate were assessed and appear in Table 2.

TABLE 2

|  | Creatine Hydrochloride | Creatine Monohydrate |
| --- | --- | --- |
| Aqueous Solubility | 679 ± 18 mg/mL | 17.9 ± 0.5 mg/mL |
| Solution pH | 0.3 | 8.6 |

Standard Solutions and Standard Curve Determination:

100 mL stock standard solutions of creatine monohydrate and creatine hydrochloride were prepared by dissolving 50 mg of the creatine derivative in 100 mL deionized water. Standard solutions of 10, 20, 30, 40, 50, and 100 µg/mL were then prepared by diluting volumes of stock solution with deionized water. Standard curves for each salt were generated by measuring the absorbance at 210 nm. A linear regression was generated and equation determined for each creatine salt with $R^2 > 0.999$ in all cases.

Saturation Solubility Determination:

Using preliminary measurements, saturated solutions of creatine monohydrate and creatine hydrochloride in deionized water were determined by adding increasing amounts of each salt to 5 mL of water in screw-capped glass bottles at 25° C. in a shaking water bath. Aliquots (5 mL) were removed after 1.5 hours, centrifuged at 3900 rpm for 10 minutes, 1 mL supernatant was diluted, and assayed spectrophotometrically at 210 nm. The mean+standard deviation of the saturation solubilities of each salt were calculated from the corresponding standard curves.

Example 3

The plasma uptake and relative bioavailability of creatine HCl and creatine monohydrate were assessed. The results appear in Table 3.

TABLE 3

|  | Creatine Hydrochloride | Creatine Monohydrate |
| --- | --- | --- |
| Average AUC | 117.4 | 82.2 |
| AUC Standard Error of the Mean (SEM) | 10.4 | 8.9 |

Bioavailability studies were performed in healthy human volunteers to compare the amount of creatine absorbed following oral administration of a 5 gram dose of either creatine monohydrate or creatine HCl. A two-arm cross-over experimental design was used in which each subject received both creatine monohydrate and creatine HCl. The order of treatment was randomly assigned and there was a 1-week wash out period between creatine treatments. Blood samples were taken immediately prior to creatine monohydrate and creatine HCl ingestion and at various time points thereafter (30-120 minutes). Plasma creatine was significantly elevated following either creatine monohydrate or creatine HCl administration. However, peak creatine plasma concentrations and plasma area under the curve (AUC) was significantly greater in the creatine HCl treatment arm.

The relative bioavailability was determined according to FDA standards for comparing a drug/nutritional supplement from two different formulations using the equation: AUC A*dose B/AUC B*dose A. The resultant relative bioavailability for creatine HC compared to creatine monohydrate was 1.65 with an SEM value of 0.12. These results suggest an approximately 50 percent increase in bioavailability for creatine HCl.

Example 4

Figure 1:
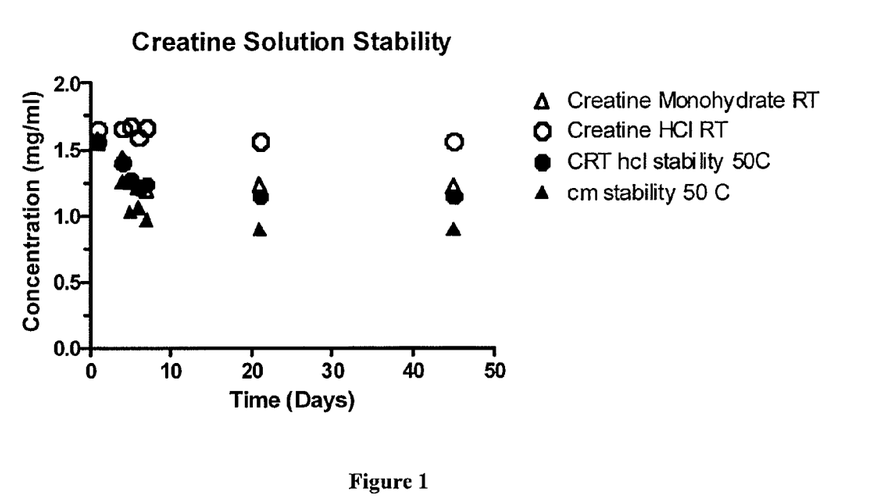
FIG. 1 is a graphical representation in linear form of the stability of creatine HCl in aqueous solution as compared to creatine monohydrate.
Figure 2:
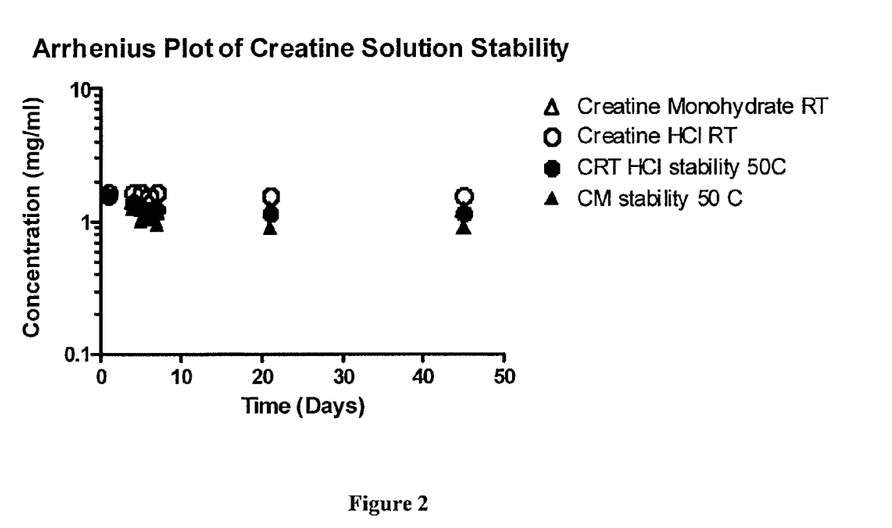
FIG. 2 is a graphical representation in log form of the stability of creatine HCl in aqueous solution as compared to creatine monohydrate.

The stability of the creatine HCl of the invention, as compared to creatine monohydrate, was tested both at room temperature (about 70° F./21° C.) and at 50° C. (122° F.). FIGS. 1 (linear data) and 2 (log scale) provide the results of this test. Each data point is representative of three different samples. Initially, each sample contained 1.5 mg/mL of creatine HCl or creatine monohydrate dissolved in aqueous solution. The creatine content of each sample was examined over a 45-day period.

As illustrated in FIGS. 1 and 2, creatine HCl demonstrated significantly greater stability compared to the creatine monohydrate samples. For example, at the end of the 45-day period, the creatine HCl sample contained approximately 95 percent of the original creatine in the aqueous solution at room temperature. Contrastingly, the creatine monohydrate sample only contained about 75 percent of the original creatine at room temperature after 45 days. For further comparison, the standard degradation time for creatine ethyl ester in water is less than one minute.

Heating the solutions resulted in an increased rate of degradation for both sample groups; however, as shown in FIGS. 1 and 2, even at 50° C., creatine HCl demonstrated superior stability in an aqueous solution compared to creatine monohydrate.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. All patents and patent applications cited in the foregoing text are expressly incorporate herein by reference in their entirety.

What is claimed is:

1. A formula comprising:
   creatine HCl, wherein the creatine HCl exhibits an aqueous solubility that is at least about 15 times greater than that of creatine monohydrate.

2. The formula of claim 1, further comprising:
   at least one additional species of creatine selected from the group comprising creatine esters, creatine pyruvate, creatine phosphate, creatine alpha-ketoglutarate, creatine citrate, and combinations thereof.

3. The formula of claim 1, further comprising:
   at least one additional supplement selected from the group comprising carbonate salts, methylsulfonylmethane, glucosamine, and chondroitin.

4. The formula of claim 1, further comprising:
   at least one compound selected from the group comprising proteins, amino acid supplements, carbohydrates, D-Ribose, fats, fiber and combinations thereof.

5. The formula of claim 1, further comprising:
   at least one sweetener selected from the group comprising sucralose, aspartame, saccharin, acesulfame potassium, neohesperidin dihydrochalcone, glycyrrhizin, thaumatin, alitame, stevioside, and combinations thereof.

6. The formula of claim 1, wherein the formula further comprises a supplement selected from the group comprising sports bars, nutritional bars, powders, liquids, gels, sports drinks, and beverages.

7. The formula of claim 1, further comprising:
   at least one flavoring agent selected from the group comprising cocoa, yogurt, peanut butter, mint, cheesecake, hazelnut paste, almonds, granola, coconut, strawberry, banana, cherry, plum, raspberry, lemon, orange, lime, pineapple, blueberry and other fruit flavors, coffee, or cremes and jellies, and combinations thereof.

8. A formula comprising:
   a first creatine having a solubility of at least about 150 mg/mL in water at 25° C. after a time period of about 1.5 hours, wherein the first creatine comprises creatine HCl.

9. The formula of claim 8, further comprising a second creatine selected from the group consisting of at least one of creatine ester, creatine pyruvate, creatine phosphate, creatine alpha-ketoglutarate, creatine citrate, and combinations thereof.

10. The formula of claim 9, wherein the first creatine comprises greater than about 50 percent of creatine in the supplement.

11. The formula of claim 8, comprised in a dietary supplement.

12. The formula of claim 10, comprised in a dietary supplement.

13. The formula of claim 8, comprised in an additive or feed supplement for livestock.

14. A formula comprising:
    creatine HCl, wherein the creatine HCl is at least 95 percent free of contaminants.

15. The formula of claim 14, comprised in a dietary supplement.

16. The formula of claim 14, wherein the dietary supplement is comprised in a sports bar, a nutritional bar, a powder, a liquid, a gel, a sports drink, a liquid meal replacement, a tablet, a dragee, a capsule, or a beverage.

* * * * *

UNITED STATES PATENT AND TRADEMARK OFFICE
CERTIFICATE OF CORRECTION

PATENT NO. : 9,486,424 B2
APPLICATION NO. : 14/629532
DATED : November 8, 2016
INVENTOR(S) : Donald W. Miller, Jonathan L. Vennerstrom and Mark C. Faulkner It is certified that error appears in the above-identified patent and that said Letters Patent is hereby corrected as shown below:

In the Claims

At Column 14, Claim 16, Line (43):
"The formula of claim 14" should be changed to "The formula of claim 15".

Signed and Sealed this
Thirty-first Day of March, 2020

Andrei Iancu
*Director of the United States Patent and Trademark Office*